(12) United States Patent
Yared et al.

(10) Patent No.: US 9,199,082 B1
(45) Date of Patent: Dec. 1, 2015

(54) DEVICES AND METHODS FOR IMPROVED PLACEMENT OF IMPLANTABLE MEDICAL DEVICES

(75) Inventors: Nadim Yared, Medina, MN (US);
Robert S. Kieval, Medina, MN (US);
Adam Cates, Delano, MN (US)

(73) Assignee: CVRx, Inc., Minneapolis, MN (US)

( * ) Notice: Subject to any disclaimer, the term of this patent is extended or adjusted under 35 U.S.C. 154(b) by 0 days.

(21) Appl. No.: 13/560,945

(22) Filed: Jul. 27, 2012

Related U.S. Application Data (60) Provisional application No. 61/512,311, filed on Jul. 27, 2011.

(51) Int. Cl.
*A61B 5/05* (2006.01)
*A61N 1/36* (2006.01)
*A61N 1/05* (2006.01)

(52) U.S. Cl.
CPC .............. *A61N 1/36117* (2013.01); *A61N 1/05* (2013.01); *A61N 1/36114* (2013.01)

(58) Field of Classification Search
USPC ........................................................ 600/411
See application file for complete search history.

(56) References Cited

U.S. PATENT DOCUMENTS

| | | | |
|---|---|---|---|
| 6,522,926 B1 | 2/2003 | Kieval et al. | |
| 6,850,801 B2 | 2/2005 | Kieval et al. | |
| 6,985,774 B2 | 1/2006 | Kieval et al. | |
| 7,480,532 B2 | 1/2009 | Kieval et al. | |
| 7,499,747 B2 | 3/2009 | Kieval et al. | |
| 7,835,797 B2 | 11/2010 | Rossing et al. | |
| 7,840,271 B2 | 11/2010 | Kieval et al. | |
| 8,086,314 B1 | 12/2011 | Kieval | |
| 2005/0153885 A1* | 7/2005 | Yun et al. ......................... 514/12 |
| 2006/0004417 A1 | 1/2006 | Rossing et al. | |
| 2006/0074453 A1 | 4/2006 | Kieval et al. | |
| 2008/0082137 A1 | 4/2008 | Kieval et al. | |
| 2009/0275956 A1* | 11/2009 | Burnes et al. .................. 606/129 |
| 2010/0004714 A1 | 1/2010 | Georgakopoulos et al. | |
| 2012/0109250 A1 | 5/2012 | Cates et al. | |
| 2012/0172680 A1* | 7/2012 | Gelfand et al. ............... 600/301 |
| 2015/0018907 A1* | 1/2015 | Razavi et al. .................. 607/116 |

* cited by examiner

*Primary Examiner* — Long V Le
*Assistant Examiner* — Kevin Pontius
(74) *Attorney, Agent, or Firm* — Patterson Thuente Pedersen, P.A.

(57) ABSTRACT

Devices and methods are provided for selecting a location to implant an electrode as part of a baroreflex activation therapy system. Images of a target blood vessel may be obtained with an imaging device, and the image used as part of or in conjunction with a patient-response-mapping procedure to determine a favorable location on the blood vessel to implant the electrode. Alternately, temperature measurements may be taken of a target vessel and utilized as part of or in conjunction with a patient-response-mapping procedure to determine a favorable location on the blood vessel to implant the electrode.

19 Claims, 3 Drawing Sheets

DEVICES AND METHODS FOR IMPROVED PLACEMENT OF IMPLANTABLE MEDICAL DEVICES

REFERENCE TO RELATED APPLICATIONS

This application claims the benefit of Provisional Patent Application No. 61/512,311, filed Jul. 27, 2011, titled "Imaging System and Method for Determining Electrode Placement," the disclosure of which is hereby incorporated by reference.

FIELD OF THE INVENTION

The present invention relates generally to implant methods and devices, and more particularly the present invention relates to improved methods and devices for implanting one or more components of a baroreflex activation device.

BACKGROUND OF THE INVENTION

Cardiovascular disease is a major contributor to patient illness and mortality. It also is a primary driver of health care expenditure, costing billions of dollars each year in the United States. Heart failure is the final common expression of a variety of cardiovascular disorders, including ischemic heart disease. It is characterized by an inability of the heart to pump enough blood to meet the body's needs and results in fatigue, reduced exercise capacity and poor survival. Heart failure results in the activation of a number of body systems to compensate for the heart's inability to pump sufficient blood. Many of these responses are mediated by an increase in the level of activation of the sympathetic nervous system, as well as by activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state. Accordingly, it is desirable to reduce the level of sympathetic nervous system activation in order to stop or at least minimize this vicious cycle and thereby treat or manage the heart failure.

Hypertension, or high blood pressure, is a major cardiovascular disorder that is estimated to affect 65 million people in the United Sates alone. Hypertension occurs when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke. Sustained high blood pressure may eventually result in an enlarged and damaged heart (hypertrophy), which may lead to heart failure.

Hypertension is a leading cause of heart failure and stroke, is the primary cause of death for tens of thousands of patients per year, and is listed as a primary or contributing cause of death for hundreds of thousands of patients per year in the U.S. Accordingly, hypertension is a serious health problem demanding significant research and development for the treatment thereof. Hypertension remains a significant risk for patients and challenge for health care providers around the world despite improvements in awareness, prevention, treatment and control over the last 30 years. Patients with hypertension are encouraged to implement lifestyle modifications including weight reduction, adopting the DASH eating plan, reducing dietary sodium, increasing physical activity, and limiting alcohol consumption and smoking A large number of pharmacologic treatments are also currently available to treat hypertension.

An improved approach for treating hypertension, heart failure and/or other cardiovascular disorders has been developed. Baroreflex Activation Therapy ("BAT") utilizes electrical, mechanical, chemical, and/or other means of stimulation to activate one or more components of a patient's baroreflex system, such as baroreceptors. Baroreceptors are sensory nerve ends that are profusely distributed within the arterial walls of the major arteries, as well in the heart, aortic arch, carotid sinus or arteries, and in the low-pressure side of the vasculature such as the pulmonary artery and vena cava. Baroreceptor signals are used to activate a number of body systems which collectively may be referred to as the baroreflex system. Baroreceptors are connected to the brain via the nervous system, allowing the brain to detect changes in blood pressure, which is indicative of cardiac output. If cardiac output is insufficient to meet demand (i.e., the heart is unable to pump sufficient blood), the baroreflex system activates a number of body systems, including the heart, kidneys, vessels, and other organs/tissues. Such natural activation of the baroreflex system generally corresponds to an increase in neurohormonal activity. Specifically, the baroreflex system initiates a neurohormonal sequence that signals the heart to increase heart rate and increase contraction force in order to increase cardiac output, signals the kidneys to increase blood volume by retaining sodium and water, and signals the vessels to constrict to elevate blood pressure. The cardiac, renal and vascular responses increase blood pressure and cardiac output, and thus increase the workload of the heart. In a patient suffering from heart failure, this further accelerates myocardial damage and exacerbates the heart failure state.

One of the first descriptions of treating hypertension through baroreceptor stimulation appears in U.S. Pat. No. 6,522,926 to Kieval et al., which discloses devices and methods for stimulating or activating baroreceptors or the baroreflex system to regulate blood pressure and/or treat other cardiovascular disorders. Generally speaking, a baroreceptor activation device may be activated, deactivated or otherwise modulated to activate one or more baroreceptors and induce a baroreceptor signal or a change in the baroreceptor signal to thereby affect a change in the baroreflex system. The baroreceptor activation device may be activated, deactivated, or otherwise modulated continuously, periodically, or episodically. The baroreceptor activation device may utilize electrical as well as mechanical, thermal, chemical, biological, or a combination thereof to activate the baroreceptor. The baroreceptor may be activated directly, or activated indirectly via the adjacent vascular tissue. Activation of this reflex increases afferent electrical signals through the carotid sinus nerve (Hering's nerve, a branch of the glossopharyngeal nerve, cranial nerve IX) to the medullary brain centers that regulate autonomic tone. Increased afferent signals to these medullary centers cause a reduction in sympathetic tone and an increase in parasympathetic tone. This results in lower heart rate, reduced sodium and water reabsorption by the kidney resulting in a diuresis, relaxation of the smooth muscle in the blood vessels which results in vasodilatation and a reduction in blood pressure. Thus, peripheral activation of the baroreflex results in a physiologic response whereby blood pressure is controlled by mechanisms determined by the integrative action of the central nervous system action on all peripheral organs and blood vessels.

The process of implanting a baroreflex activation device for delivering baroreflex therapy, such as an electrode assembly, involves "mapping"—positioning the assembly such that the electrodes are properly situated against the arterial wall of a vessel containing baroreceptors, and securing the electrode assembly to the artery so that the positioning is maintained.

Mapping adds to the overall procedure time due to adjusting and re-adjusting the position of the electrode assembly during implantation. Present-day procedures involve positioning and holding the electrode assembly in place with forceps, hemostat or similar tool while applying the stimulus and observing the response in the patient. Movement by as little as 1 mm can make a medically relevant difference in the effectiveness of the baroreceptor activation.

The positioning is a critical step, as the electrodes must direct as much energy as possible toward the baroreceptors for maximum effectiveness and efficiency. The energy source for the implanted baroreflex stimulation device is typically an on-board battery with finite capacity, and it is desirable to provide a lower energy source to ensure patient safety. A high-efficiency implantation will provide a longer battery life and correspondingly longer effective service life between surgeries because less energy will be required to achieve the needed degree of therapy. As such, during implantation of the electrode assembly, the position of the assembly is typically adjusted several times during the implantation procedure in order to optimize the baroreflex response. One example of mapping methods and techniques for implanting electrodes is disclosed in U.S. Pat. No. 6,850,801 to Kieval et al.

Although this approach is effective, it can prove to be time consuming and invasive. One of the many challenges related to the mapping process is keeping track of previous desirable positions. Because positioning the electrode assembly is an optimization procedure, surgeons will tend to search for better positions until they have exhausted all reasonable alternative positions. Returning the electrode assembly to a previously-observed optimal position can be quite difficult and frustrating, especially under surgical conditions. Further, a large incision is necessary for the mapping procedure described in the '801 patent, in order to provide clearance for positioning and re-positioning of the electrode assembly.

Therefore, a need exists for improved devices and methods of determining an optimal electrode location that are more repeatable, more precise, less time-consuming and less invasive than current methods.

SUMMARY OF THE INVENTION

In one embodiment, the present invention is a method of implanting an electrode, comprising obtaining an image of a blood vessel of a patient with an imaging device, delivering electrical signals to the blood vessel from two or more locations, measuring a patient response to the delivery of each electrical signal at each of the two or more locations, generating an indication on the image of the locations of the delivered signals and the measured patient responses, and selecting, based on the indication, a suitable location to implant a therapy device.

In another embodiment, the present invention is an implantable baroreflex activation system, comprising a control system having an implantable housing, means for measuring temperature, and an electrode structure proximate a distal end of the electrical lead, the electrode structure including an electrode, a backing material, and a means for interfacing with an implant tool positionable proximal of the backing material, wherein the electrode structure is configured for implantation on an outer surface of a blood vessel at a location determined based on a plurality of temperature measurements obtained from the means for measuring temperature, and wherein the control system is programmed to deliver a baroreflex therapy via the monopolar electrode to a baroreceptor within a wall of the blood vessel.

In a further embodiment, the present invention is a method of implanting a baroreflex activation system, comprising creating an incision in a patient, obtaining a plurality of temperature measurements of the area of a desired implant location, releasably coupling an electrode structure to an implant tool, the electrode structure including an electrode, a backing material, and a means for releasably interfacing with the implant tool, selecting a suitable implant location for the electrode structure based on the plurality of temperature measurements, securing the electrode structure at the implant location such that the monopolar electrode is in contact with an outer surface of the blood vessel, implanting the housing, and connecting the electrode structure to the control system with the electrical lead.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Embodiments of the present invention generally pertain to devices and methods for determining a suitable location on a blood vessel for implanting one or more electrodes as part of a baroreflex activation therapy system. In one embodiment, an image of the blood vessel may be obtained, which is then utilized in conjunction with a patient-response-mapping procedure, to locate, record and/or determine a suitable location for implanting the one or more electrodes within the patient. In another embodiment, thermal measurements are obtained of multiple points on a blood vessel, and the measurements are utilized to locate, record and/or determine a suitable location for implanting the one or more electrodes. Optionally, an image of the blood vessel may be used in conjunction with the thermal measurements. As used herein, an image may comprise a picture, a graphic representation, computer-generated or otherwise, and any other representation or indication of the appearance and/or form of the target object, in this case a blood vessel.

Baroreceptor signals in the arterial vasculature are used to activate a number of body systems which collectively may be referred to as the baroreflex system. For the purposes of the present invention, it will be assumed that the "receptors" in the venous and cardiopulmonary vasculature and heart chambers function analogously to the baroreceptors in the arterial vasculature, but such assumption is not intended to limit the present invention in any way. In particular, the methods described herein will function and achieve at least some of the stated therapeutic objectives regardless of the precise and actual mechanism responsible for the result. Moreover, the present invention may activate baroreceptors, mechanoreceptors, pressoreceptors, stretch receptors, chemoreceptors, or any other venous, heart, or cardiopulmonary receptors which affect the blood pressure, nervous system activity, and neurohormonal activity in a manner analogous to baroreceptors in the arterial vasculation. For convenience, all such venous receptors will be referred to collectively herein as "baroreceptors" or "receptors" unless otherwise expressly noted.

While there may be small structural or anatomical differences among various receptors in the vasculature, for the purposes of some embodiments of the present invention, activation may be directed at any of these receptors and/or nerves and/or nerve endings from these receptors so long as they provide the desired effects. In particular, such receptors will provide afferent signals, i.e., signals to the brain, which provide the blood pressure and/or volume information to the brain. This allows the brain to cause "reflex" changes in the autonomic nervous system, which in turn modulate organ activity to maintain desired hemodynamics and organ perfusion. Stimulation of the baroreflex system may be accomplished by stimulating such receptors, nerves, nerve fibers, or nerve endings, or any combination thereof.

For additional information pertaining to the cardiovascular, circulatory and nervous systems, as well as baroreceptor and baroreflex therapy systems that may be used in whole or in part with embodiments of the present invention, reference is made to the following commonly assigned published applications and patents: U.S. Published Patent Application Nos. 2006/0004417 to Rossing et al., 2006/0074453 to Kieval et al., 2008/0082137 to Kieval et al., 2010/0004714 to Georgakopoulos et al., and 2012/0109250 to Cates et al., and U.S. Pat. No. 6,522,926 to Kieval et al., U.S. Pat. No. 6,850,801 to Kieval et al., U.S. Pat. No. 6,985,774 to Kieval et al., U.S. Pat. No. 7,480,532 to Kieval et al., U.S. Pat. No. 7,499,747 to Kieval et al., U.S. Pat. No. 7,835,797 to Rossing et al., U.S. Pat. No. 7,840,271 to Kieval et al., and U.S. Pat. No. 8,086,314 to Kieval, the disclosures of which are hereby incorporated by reference in their entireties except for the claims and any expressly contradictory definitions.

Pre-Operative Imaging Procedure

In one embodiment, the present invention provides a system that is configured to obtain one or more visual images (one, two, or three-dimensional) of the carotid sinus (or other target baroreceptor vessels), apply an electrical signal that activates baroreceptors, measure a response of the patient to the signal, collect and analyze the patient data, and convert the one or more images and the patient response into a visual display or index to guide the implant physician to an optimal location for the electrode. There may additionally or in the alternative be an audible feedback signal used to indicate the optimal location for electrode placement based on the obtained data. The image or patient response map can be used both in order to plan the implantation of a medical device (for example by testing response of the patient to assess the usefulness of the device for that particular patient) as well as guide the physician in the course of carrying out the implant procedure (for example by finding the most effective placement location of the device).

The image of a blood vessel may be obtained in a separate procedure prior to implanting an electrode. Such a pre-operative procedure may include the use of magnetic resonance imaging (MRI), magnetic resonance angiography, fluoroscopy, projection radiography, x-ray computed tomography, optical coherence tomography, ultrasound, magnetic field positioning, or acoustic waves. Image registration techniques may be applied to images obtained through these means, for example during a later electrode mapping and implant procedure. Registration is the process of transforming different sets of data into one coordinate system. Data may include images, data obtained from various sensors, data obtained at different times, or from different viewpoints. Registration is necessary in order to be able to compare or integrate the data obtained from these different measurements. In the present invention, registration may be necessary in order to compare or integrate data obtained from these different images and measurements and may include without limitation multiple images from different sources or imaging techniques and measured patient parameters from different sensors.

In one embodiment, optical coherence tomography (OCT) may be utilized to obtain an image of a blood vessel. OCT has previously been known for identifying plaque in blood vessels. Optical coherence tomography utilizes optical signals (in the form of near-infrared light having relatively long wavelengths) to generate a three-dimensional image from within biological tissue. An imaging probe may be provided in the form of an optical, light-emitting probe that employs one or more sources, such as superluminescent diodes, ultrashort pulsed lasers and supercontinuum lasers.

In one embodiment, magnetic field positioning may be utilized to obtain an image of a blood vessel, such as the CARTO mapping and navigation system available from Biosense Webster, Inc. The CARTO system uses static magnetic fields that are calibrated and computer controlled. The CARTO system includes four parts—a reference device, position sensor, decoder, and computer data analyzer. The reference device contains a ring of magnets with different magnetic fields placed in different locations. The position sensor detects the characteristics of the magnets and transmits the signals to the decoding unit. The decoder calculates the position and orientation of the magnets. The position sensor usually includes two sensors, one located in the tip of a catheter and a second located on or in a patient. Due to the nature of magnetic fields, the orientation may also be calculated while the tip is stationary. By calculating the strength and orientation of the magnetic fields at a given location, the x, y, and z position may be calculated along with the roll, pitch, yaw orientation.

The use of two sensors allows the system to calculate the relative position of the catheter tip. The signals received from the sensors are converted and calculated to provide information, such as the position, orientation, temperature and other patient values. The data from the decoder is interpreted by the computer and projected onto a pre-acquired CT and a map is generated. A catheter-type instrument may be provided, which includes magnets and one or more electrodes for conducting a mapping procedure. Additionally, a position module is provided including at least two sensors configured to detect the magnets characteristics on the instrument, and the characteristics are converted and interpreted by the system to provide image data in the form of a display of the target blood vessel. This data can be added to information obtained during a mapping procedure to provide an image of the target vessel along with the patient response information.

In one embodiment, ultrasound may be utilized to obtain an image of a blood vessel. For example, a carotid duplex is a carotid ultrasonography performed using by duplex ultrasonography, which combines B-mode imaging (which provides images of various levels, or planes, enabling the creation of a three-dimensional image of the carotid artery wall and surround structures) and Doppler spectrum analysis, to detect and assess carotid occlusive disease.

Once an image has been obtained through one of the above methods, registration techniques may be utilized in order to make use of the image during a subsequent patient-response-mapping and implant procedure. Such a patient-response-mapping procedure generally involves positioning an electrode at a location on a blood vessel containing baroreceptors, applying an electrical signal via the electrode, measuring and logging a patient response to the electrical signal, and then repeating the process at subsequent locations on the vessel. In one embodiment, the mapping procedure may be as described in U.S. Published Patent Application No. 2012/0109250 to Cates et al., previously incorporated by reference above.

Patient physiological responses that may be measured during a mapping procedure include blood pressure, heart rate, cardiac output, stroke volume or other cardiac parameters, EEG, respiration parameters, pulse oximetry, intrinsic nerve activity, vessel wall acceleration or other vessel wall motion measurements, reflected arterial pressure waves, indices of vascular stiffness, direct measures of sympathetic and parasympathetic nervous system activity, plasma concentrations of neurohormones or other biomarkers, for example.

Figure 1:
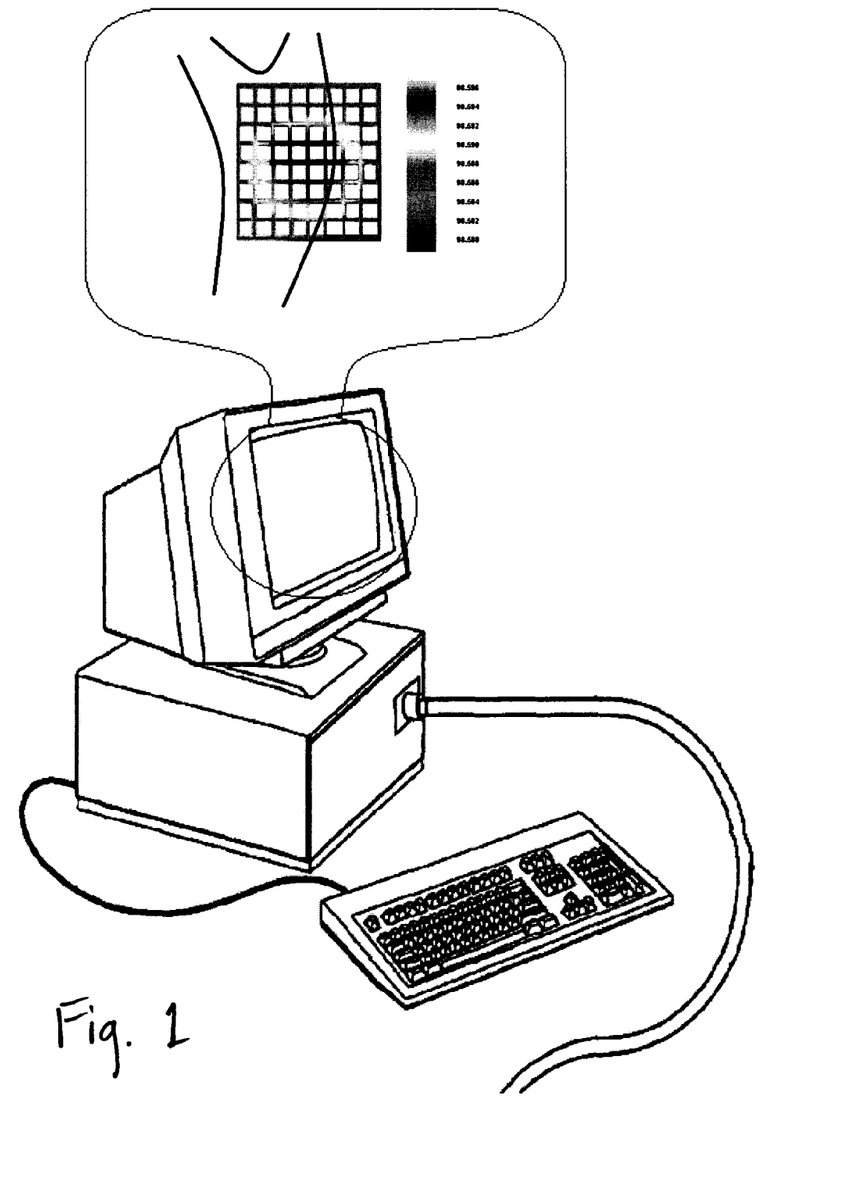
FIG. 1 is a schematic representation of an image display arrangement according to an embodiment of the present invention.

The mapping instrument may include a GPS-based sensor to track position during the procedure, such that the location of the instrument can be correlated with a displayed image of the target blood vessel. A display may be provided which projects the previously-obtained image of the blood vessel during the mapping procedure, such as in FIG. 1. As signals are delivered and patient responses measured, that information is added to the display. In one embodiment, the information may be presented in the form of a color scale, with different colors representing different levels of measured responses such that the surgeon visually sees a color index indicating the response to stimulation along the vessel (for example, red being the greatest response, orange, yellow, green, and blue being the least response). The location with the most red/orange would indicate to the physician the best location for placement of the electrode. In another embodiment, the information may be presented as numerical data. Additionally, numerical data may be combined with a color scale representation. In another embodiment, an audible response or indication is provided as part of the mapping procedure.

Once the surgeon has mapped a sufficient number of data points, the display is reviewed and relied upon to determine the location of an optimal patient response. Most typically, the location of optimal patient response will be the location at which a therapy electrode is chronically implanted. However, in another embodiment unfavorable responses are also measured as part of the mapping process, and these unfavorable responses are taken into account when determining where to chronically implant a therapy electrode. For example, unfavorable responses may include for example an undesirable change in patient hemodynamics (increased blood pressure or reduced cardiac output), the sensation of pain, paresthesia or other sensed measurement related to extraneous nerve stimulation such as muscle spasm, tightness, coughing, respiration change, voice change, and so forth. By considering unfavorable responses as part of the mapping procedure, a chronic electrode implant location may be determined based not only on a measured favorable response, but also a measured unfavorable response. The selected location may not represent the best favorable response, but rather a balance between measured favorable responses and measured unfavorable responses.

Figure 2A:
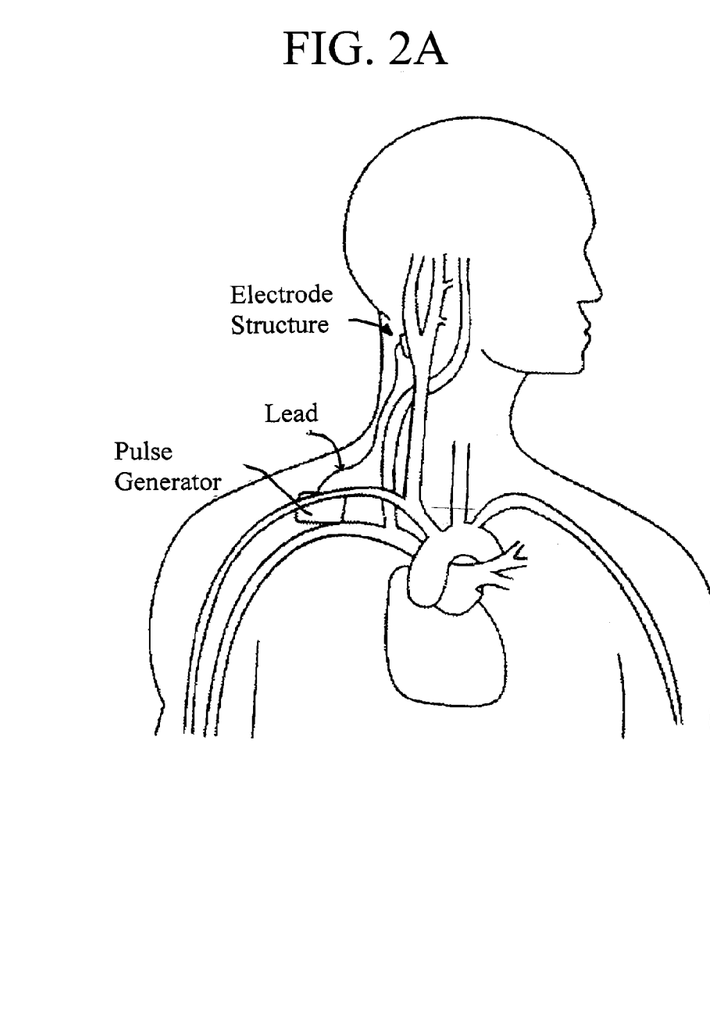
FIGS. 2A and 2B are schematic representations of a baroreflex activation system according to an embodiment of the present invention implanted on a carotid sinus within a patient.
Figure 2B:
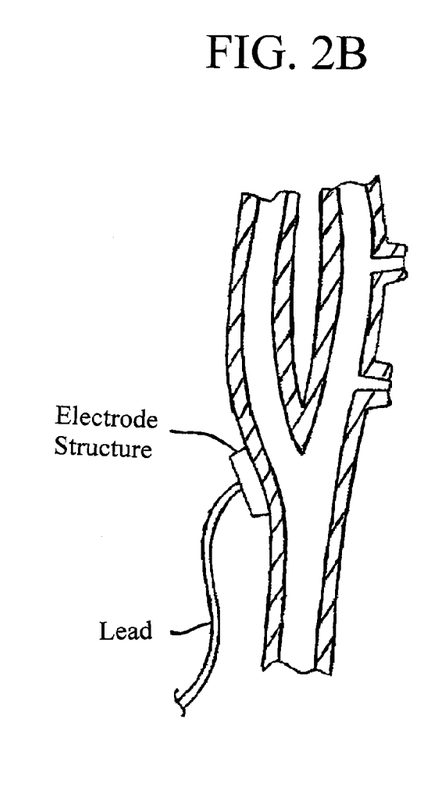
Figure 3:
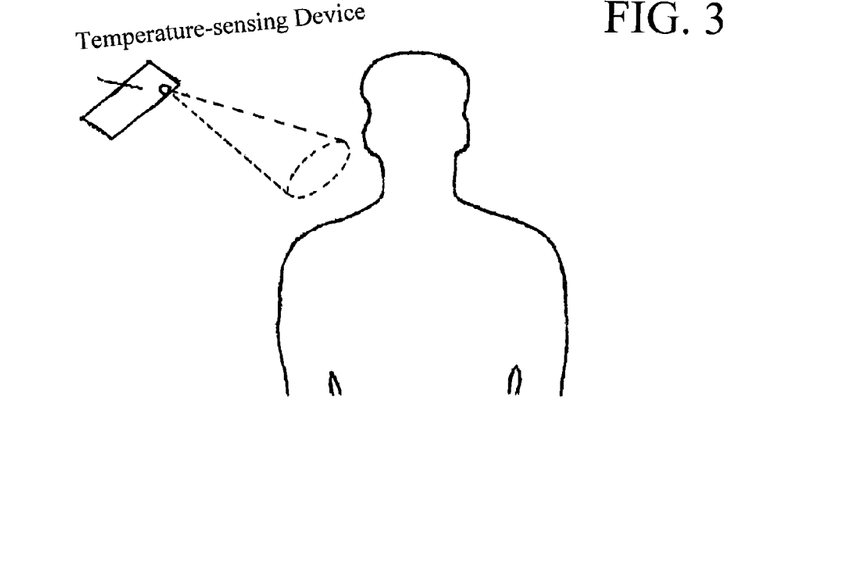
FIG. 3 is a schematic representation of a stand-alone temperature-sensing device according to an embodiment of the present invention.
Figure 4:
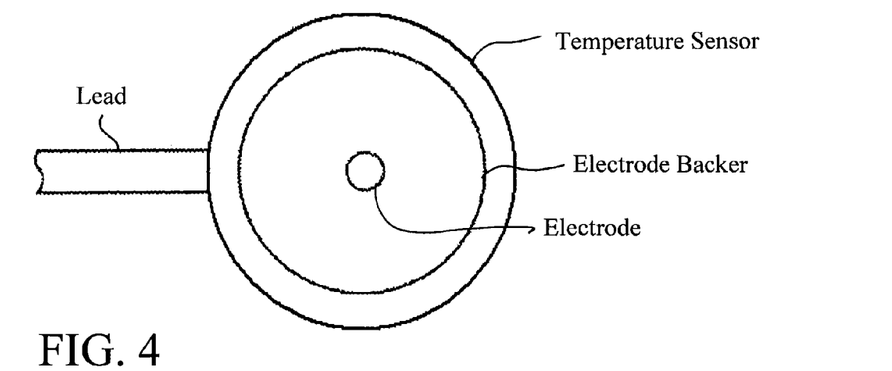
FIG. 4 is a plan view of an electrode structure having an integrated temperature sensor, according to an embodiment of the present invention.

In one embodiment, the mapping procedure is conducted using the same electrode structure that will be implanted chronically. Once the desired location has been determined through the patient-response-mapping procedure and vessel image information, the electrode structure, lead, pulse generator (control system) and any other associated devices are implanted according to known procedures, such as in FIGS. 2A and 2B. In another embodiment, wherein the mapping procedure is conducted with a separate electrode and/or apparatus, the devices used for mapping are withdrawn and the therapy electrode structure, lead, and pulse generator are implanted according to known procedures. Usage of location-tracking capabilities such as GPS may be utilized in conjunction with implanting the therapy electrode, in order to insure the therapy electrode is positioned at the precise desired location as determined through the mapping procedure. For example, the electrode structure or the delivery tool may include GPS capabilities. Optionally, visual or audible guidance is provided to assist the surgeon in location the predetermined desired implant location.

Concurrent Imaging Procedure

In another embodiment, the present invention comprises devices and methods configured for obtaining an image of a blood vessel as part of a mapping procedure. The imaging device may be separate from, or combined with, a therapy/mapping device. Imaging may be conducted intravascularly, extravascularly such as directly on a vessel, or on or proximate the skin of the patient. The image of a blood vessel may be obtained through the use of intravascular ultrasound, ultrasound Doppler, fluoroscopy, infrared imaging, or other procedures. Image registration may or may not be necessary to coordinate the vessel image(s) with a patient-response-mapping procedure. For example, where more than one image is relied upon, or where the procedure depends upon a dynamic reference, registration techniques may be required in order to combine data from all resources. The overall procedure includes obtaining one or more images of a target blood vessel, then applying an electrical therapy signal with the one or more mapping/therapy electrode(s) to a patient at the location of baroreceptors, measuring a hemodynamic response of the patient with a sensor, registering the data if necessary or desired, and providing a visual or audible index of the patient response to the electrical therapy in connection with the obtained three-dimensional image of the blood vessel, in order to best find the optimal location to implant a medical device on, in or proximate the blood vessel.

Because the data collected from various sources may not be geometrically aligned, the image-guided system of the invention in some embodiments may require a plurality of references for registration purposes, to align the images with the data collected. In one embodiment, one reference may be placed about the patient, while the other is placed on or incorporated with the delivery tool or electrode. The references are then used to align the measured data with the images collected.

In one embodiment, intravascular ultrasound (IVUS) may be used to obtain a blood vessel image. An ultrasound catheter is delivered into the vasculature and advanced to the target blood vessel. Sound waves are emitted from the ultrasound catheter (usually in the 20-40 MHz range), and the catheter receives and then conveys the return echo information to an external computer which displays the ultrasound image of a thin section of the blood vessel. This technique can differentiate blood and tissue from heavier calcium deposits and the like. The image of the target vessel will show the lumen of the vessel, including any bifurcations such as in the carotid artery.

In one embodiment, ultrasound Doppler may be utilized to obtain an image of a blood vessel. Ultrasound Doppler emits sound waves and measures returning echo waves to determine how far away an object is, along with its size, shape and consistency. Because ultrasound Doppler can determine whether the object is solid or fluid, it is commonly used to evaluate blood flow through a blood vessel. In the present invention however, ultrasound Doppler may be used as a way to acquire an image from the exterior of the vessel. In this embodiment, the imaging device includes a catheter with an ultrasound transducer at the tip. The catheter is placed about the vessel to acquire an image of the vessel.

In another embodiment, infrared imaging (or thermal imaging) is utilized to create a visual representation of a blood vessel. In this embodiment, an infrared camera is placed about the target vessel. The camera forms an image using infrared radiation and is able to distinguish temperature variations along the vessel and create a visual, colored display of the warmest location, thus the site of the baroreceptors. Because the vessel wall may be thinner in areas having higher concentrations of baroreceptors, a higher measured temperature may be indicative of a thinner blood vessel wall (due to the warm blood being closer to the outer surface) and therefore indicative of a greater concentration of baroreceptors, making it a suitable location for implanting a therapy electrode. For example, a thermogram may be created based on the heat of the blood pumping through the blood vessel. This image may then be used during a patient-response-mapping procedure. By way of example, temperature variations are shown in colors, while mapping response is shown by contrast or textures.

Generally, in an example procedure, a physician would make a small incision, such as a percutaneous incision on the side of the neck at the location of the carotid sinus. An imaging instrument is fed to the sinus, and the imaging process is conducted. Optionally, additional images may be obtained separately through other means prior to implant such as MRI or CT, in which case the two or more images may be registered to transform the different images into one coordinate system, thereby aligning the various points from multiple images and providing spatial arrangement between the anatomical features and measured physiological data. Methods of automatic, semiautomatic or manual/interactive registration may be used depending on the data obtained and the implant physician's choice.

Once an image has been obtained through one of the above methods, registration techniques may be utilized as necessary during the mapping procedure to align the image with measured patient responses. Such a patient-response-mapping procedure generally involves positioning an electrode at a location on a blood vessel containing baroreceptors, applying an electrical signal via the electrode, measuring and logging a patient response to the electrical signal, and then repeating the process at subsequent locations on the vessel. In one embodiment, the mapping procedure may be as described in U.S. Published Patent Application No. 2012/0109250 to Cates et al., previously incorporated by reference above.

Patient physiological responses that may be measured during a mapping procedure include blood pressure, heart rate, cardiac output, stroke volume or other cardiac parameters, EEG, respiration parameters, pulse oximetry, intrinsic nerve activity, vessel wall acceleration or other vessel wall motion measurements, reflected arterial pressure waves, indices of vascular stiffness, direct measures of sympathetic and parasympathetic nervous system activity, plasma concentrations of neurohormones or other biomarkers, for example.

The therapy/mapping instrument may include a GPS-based sensor to track position during the procedure, such that the location of the instrument can be correlated with a displayed image of the target blood vessel. For example, GPS capabilities may be incorporated into an electrode backer or into a delivery tool used during the procedure. A display may be provided which projects the previously-obtained image of the blood vessel during the mapping procedure. As signals are delivered and patient responses measured, the response information is added to the image display. In one embodiment, the information may be presented in the form of a color scale, with different colors representing different levels of measured responses such that the surgeon visually sees a color index indicating the response to stimulation along the vessel (for example, red being the greatest response, orange, yellow, green, and blue being the least response). The location with the most red/orange would indicate to the physician the best location for placement of the electrode. In another embodiment, the information may be presented as numerical data. Additionally, numerical data may be combined with a color scale representation.

Once the surgeon has mapped a sufficient number of data points, the display is reviewed and relied upon to determine the location of an optimal patient response. Most typically, the location of optimal patient response will be the location at which a therapy electrode is chronically implanted. However, in another embodiment unfavorable responses are also measured as part of the mapping process, and these unfavorable responses are taken into account when determining where to chronically implant a therapy electrode. For example, unfavorable responses may include for example an undesirable change in patient hemodynamics (increased blood pressure or reduced cardiac output), the sensation of pain, paresthesia or other sensed measurement related to extraneous nerve stimulation such as muscle spasm, tightness, coughing, respiration change, voice change, and so forth. By considering unfavorable responses as part of the mapping procedure, a chronic electrode implant location may be determined based not only on a measured favorable response, but also a measure unfavorable response. The selected location may not represent the best favorable response, but rather a balance between measured favorable responses and measured unfavorable responses.

In one embodiment, the mapping procedure is conducted using the same electrode structure that will be implanted chronically, i.e., the therapy electrode. Once the desired location has been determined through the mapping procedure and vessel image information, the electrode structure, lead, pulse generator (control system) and any other associated devices are implanted according to known procedures. In another embodiment, wherein the mapping procedure is conducted with a separate electrode and/or apparatus, the devices used for mapping are withdrawn and the therapy electrode structure, lead, and pulse generator are implanted according to known procedures. In one embodiment, the mapping and imaging can be performed with one device, while the therapy device is separate and configured to be implanted chronically. Usage of location-tracking capabilities such as GPS may be utilized in conjunction with implanting the therapy electrode, in order to insure the therapy electrode is positioned at the precise desired location as determined through the mapping procedure. Optionally, visual or audible guidance is provided to assist the surgeon in location the predetermined desired implant location.

In an alternate embodiment, imaging is utilized to confirm an electrode placement determined through a patient-response-mapping procedure. For example, a patient-response-mapping procedure is conducted as described herein, either with the benefit of a registered blood vessel image or without. Subsequent to determining a suitable implant location for the electrode, a confirmatory image is obtained, to verify suitable placement of the electrode. In one embodiment, intravascular ultrasound, as described herein, is utilized to obtain a vessel image. An intravascular ultrasound image can provide verification that the electrode has been placed or implanted at a location with favorable concentration of baroreceptors, by depicting a change in tissue appearance in the wall of the vessel where baroreceptors are located.

Temperature-Based Determination of Electrode Location

In other embodiments, the present invention comprises systems and methods for electrode placement based on temperature measurements of a subject blood vessel. The inventors of the present application theorize that greater concentrations of baroreceptors can be found where a vessel wall is relatively thinner. Because baroreceptors are stretch receptors naturally activated by pressure pulses within a blood vessel, being located in thinner (and therefore more distensible) portions of a vessel wall may increase the natural effectiveness of the baroreceptors. By measuring the temperature of a blood vessel surface at many different locations, variations in temperature readings may be observed, with higher measured temperatures indicating thinner vessel wall portions, and therefore greater concentrations of baroreceptors and/or baroreceptors having greater sensitivity. Once a favorable location has been found through such temperature measurements, one or more therapy electrodes may be implanted at this location in order to achieve an optimal response from a delivered electrical therapy.

Therefore, it is recognized that there is a relationship between vessel thickness or thinness, vessel movement (stretch and/or elasticity) and baroreceptor sensitivity or quantity. Thus, in one embodiment, the system uses one or more of these measured inputs of vessel movement, vessel wall thickness and/or baroreceptor sensitivity or quantity, to place the device. One or more of these measurements may also be used to derive the others.

These measurements may also be used to generate a visual display for placement of the electrodes. For example, the temperature measurements may be collected, processed, and converted into a tangible form such as a visual image display or auditory signal, which indicates warmer or warmest locations of the blood vessel, and therefore a favorable location to implant an electrode. The temperature data may also be transmitted to a system that collects images of the vessel (such as CT, MRI, etc.) to be registered along with other patient data such as blood pressure or other physiological data.

In one embodiment, a system may be provided including a thermal measurement device coupled with an electrode placement tool. For example, the system could consist of a catheter-based system that includes thermal sensing and/or imaging and mapping capability. The thermal measurement device could be used by either placing it directly on the exterior of the vessel through an incision in the skin, or in close proximity to the vessel via a percutaneous approach. In another embodiment, temperature measurements may be obtained with a stand-alone device.

Alternatively, temperature sensing means may be included as part of an electrode structure configured for chronic implant. For example, the temperature sensing means may be incorporated into the base material of an electrode structure, for example as an additional backer, or the temperature sensing means may be incorporated into the existing backer.

In operation, the temperature measurement device is moved around a blood vessel and the obtained temperature measurements are transmitted to a computer or other processor. The processor analyzes the temperature measurements and displays the data as, for example, a color-coded image. The color can be displayed as a cartoon-like image using a representative vessel, indicating the warmest spot along the vessel which is thus the most concentrated location of the baroreceptors. In another embodiment, the temperature measurements can be used in connection with an image obtained through other imaging techniques discussed herein (CT, ultrasound, MRI, etc.) and the measurements aligned to an actual anatomical image of the patients carotid sinus using registration techniques described in the first embodiment above.

In another embodiment, an algorithm and computer program are provided for collecting and analyzing vessel temperature measurements, and providing an index relative to patient vessel wall thickness. This index can be a chart, thermal image (red being the warmest and thus the highest concentration of baroreceptors), or an auditory signal (a higher pitch for a warmer temperature). If patient-response-mapping is also performed, the algorithm may include steps for analyzing response of the patient in combination with the temperature measurement, to find the optimal location based on both measures. In such case, the color display or auditory feedback would indicate the best position using both inputs.

Electrode Migration

One possible drawback to implantable electrical devices is that electrodes can migrate over time, away from the intended target. This may be caused by patient activity, implant fixation error, or just over time as the vessel pulses. To address this phenomenon, an array electrode may be desirable, along with use of electromagnetic or other movement-sensing device. For example, a physician may track the patient response and potential movement of the electrode and if the response declines because movement occurs, the physician may switch the between the various electrodes on the array in order to change the output location to a more effective target along the vessel. In this type of procedure, during implant, a movement-sensing system is also implanted. For example, electromagnetic particles that transmit radiofrequency waves are implanted proximate the electrode. For example, these EM particles may be incorporated into the electrode base. During implant, the physician uses the system to transmit RF signals from the particles to an EM array that generates the position of the particles/electrode. In a follow-up to implant procedure, the physician uses a RF receiver to determine the current coordinates of the particles (which corresponds to the location of the electrode), and thereby determining based on the location at implant, whether there was movement of the electrode. The physician can then use the programmer to change the electrode output, measure response and set the new electrode parameters.

Various modifications to the embodiments of the inventions may be apparent to one of skill in the art upon reading this disclosure. For example, persons of ordinary skill in the relevant art will recognize that the various features described for the different embodiments of the inventions can be suitably combined, un-combined, and re-combined with other features, alone, or in different combinations, within the spirit of the invention. Likewise, the various features described above should all be regarded as example embodiments, rather than limitations to the scope or spirit of the inventions. Therefore, the above is not contemplated to limit the scope of the present inventions. Although described mainly in the context of electrical activation of baroreceptors for mapping and chronic therapy, alternate means of activation may also be utilized, such as localized pressure or suction, chemical activation, thermal activation, optical activation, mechanical activation, or other means of activation such as described in the patents and publications incorporated by reference herein.

Persons of ordinary skill in the relevant arts will recognize that the inventions may comprise fewer features than illustrated in any individual embodiment described above. The embodiments described herein are not meant to be an exhaustive presentation of the ways in which the various features of the inventions may be combined. Accordingly, the embodiments are not mutually exclusive combinations of features; rather, the inventions may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the embodiments of the present inventions, it is expressly intended that the provisions of Section 112, sixth paragraph of 35 U.S.C. are not to be invoked unless the specific terms "means for" or "step for" are recited in a claim.

The invention claimed is:

1. A method comprising:
   obtaining an image of a blood vessel of a patient with an imaging device;
   delivering an electrical signal to the blood vessel from two or more locations;
   measuring a patient response to the delivery of each delivered electrical signal at each of the two or more locations;
   generating an indication on the image of the location of a plurality of delivered signals and generating an indication of the measured patient response for each delivered signal so as to create a map on the image of the blood vessel including the plurality of indications of delivered electrical signals and measured patient responses; and
   selecting, based on the map on the image of the blood vessel, a suitable location to implant an electrode.

2. The method of claim 1, further comprising registering the image and the patient responses to provide a visual indication of patient responses based on location.

3. The method of claim 1, wherein obtaining an image of a blood vessel of a patient with an imaging device comprises obtaining an image with optical coherence tomography.

4. The method of claim 1, wherein obtaining an image of a blood vessel of a patient with an imaging device comprises obtaining an image with magnetic resonance imaging.

5. The method of claim 1, wherein obtaining an image of a blood vessel of a patient with an imaging device comprises obtaining an image with ultrasound.

6. The method of claim 1, wherein obtaining an image of a blood vessel and delivering electrical signals to the blood vessel are performed by the same device.

7. The method of claim 6, wherein measuring a patient response, obtaining an image of a blood vessel and delivering electrical signals to the blood vessel are all performed by the same device.

8. A method comprising:
   obtaining an image of a blood vessel of a patient with an imaging device;
   delivering an electrical signal to the blood vessel from a first location;
   measuring a patient response to the electrical signal delivered from the first location;
   generating an indication on the image of the location of the electrical signal delivered from the first location and of the measured patient response associated with the first location;
   delivering an electrical signal to the blood vessel from a second location;
   measuring a patient response to the electrical signal delivered from the second location;
   adding an indication on the image of the location of the electrical signal delivered from the second location and of the measured patient response associated with the second location, so as to create a depiction on the image of the blood vessel of a plurality of indications of delivered electrical signals and associated measured patient responses; and
   selecting, based on the indications, a suitable location to implant an electrode.

9. The method of claim 8, further comprising registering the image and the patient responses for each delivered signal to provide a visual indication of patient responses based on location.

10. The method of claim 8, wherein obtaining an image of a blood vessel of a patient with an imaging device comprises obtaining an image with optical coherence tomography.

11. The method of claim 8, wherein obtaining an image of a blood vessel of a patient with an imaging device comprises obtaining an image with magnetic resonance imaging.

12. The method of claim 8, wherein obtaining an image of a blood vessel of a patient with an imaging device comprises obtaining an image with ultrasound.

13. The method of claim 8, wherein obtaining an image of a blood vessel and delivering electrical signals to the blood vessel are performed by the same device.

14. The method of claim 13, wherein measuring a patient response, obtaining an image of a blood vessel and delivering electrical signals to the blood vessel are all performed by the same device.

15. A method comprising:
   obtaining an image of a blood vessel of a patient with an imaging device;
   delivering an electrical signal to the blood vessel from two or more locations;
   measuring a patient response to the delivery of each delivered electrical signal at each of the two or more locations;

generating a collection of indications on the image of a plurality of locations of the delivered signals and the measured patient responses; and selecting, based on the collection of indications, a suitable location to implant an electrode.

16. The method of claim 15, further comprising registering the image and the patient responses to provide a visual indication of patient responses based on location.

17. The method of claim 15, wherein obtaining an image of a blood vessel of a patient with an imaging device comprises obtaining an image with a technique selected from the group consisting of optical coherence tomography, magnetic resonance imaging and ultrasound.

18. The method of claim 15, wherein obtaining an image of a blood vessel and delivering electrical signals to the blood vessel are performed by the same device.

19. The method of claim 18, wherein measuring a patient response, obtaining an image of a blood vessel and delivering electrical signals to the blood vessel are all performed by the same device.

* * * * *